(12) United States Patent
Krog

(10) Patent No.: US 11,925,182 B2
(45) Date of Patent: Mar. 12, 2024

(54) DETECTING SURFACE CHARACTERISTICS OF FOOD OBJECTS

(71) Applicant: MAREL SALMON A/S, Stovring (DK)

(72) Inventor: Carsten Krog, Aalborg (DK)

(73) Assignee: MAREL SALMON A/S, Stovring (DK)

( * ) Notice: Subject to any disclaimer, the term of this patent is extended or adjusted under 35 U.S.C. 154(b) by 626 days.

(21) Appl. No.: 17/253,010

(22) PCT Filed: Jul. 1, 2019

(86) PCT No.: PCT/EP2019/067625
§ 371 (c)(1),
(2) Date: Dec. 16, 2020

(87) PCT Pub. No.: WO2020/007804
PCT Pub. Date: Jan. 9, 2020

(65) Prior Publication Data
US 2021/0112818 A1  Apr. 22, 2021

(30) Foreign Application Priority Data
Jul. 2, 2018  (EP) ..................................... 18181211

(51) Int. Cl.
*G06T 7/00* (2017.01)
*A22B 5/00* (2006.01)
(Continued)

(52) U.S. Cl.
CPC ............ *A22B 5/007* (2013.01); *A22C 17/008* (2013.01); *G01N 33/12* (2013.01); *G06T 7/0004* (2013.01); *G06T 2207/30128* (2013.01)

(58) Field of Classification Search
CPC ... A22B 5/007; A22C 17/008; A22C 17/0073; A22C 17/0086; G01N 33/12; G06T 7/0004; G06T 2207/30128
See application file for complete search history.

(56) References Cited

U.S. PATENT DOCUMENTS

| 4,529,316 A | 7/1985 | Dimatteo |
| 5,642,198 A | 6/1997 | Long |

(Continued)

FOREIGN PATENT DOCUMENTS

WO   2008016309 A1   2/2008

OTHER PUBLICATIONS

Extended Search Report and Written Opinion from European Application No. EP18181211, dated Dec. 19, 2018.
(Continued)

*Primary Examiner* — Van D Huynh
(74) *Attorney, Agent, or Firm* — Workman Nydegger

(57) ABSTRACT

An apparatus for detecting surface characteristics on food objects conveyed by a conveyor has a first imaging device for capturing two-dimensional image data (2D) and a second imaging device for capturing three-dimensional image data (3D) of a food object. A image processing unit is configured to utilize either the 2D or 3D image data in determining whether a potential defect is present on the surface of the food object. The image processing unit determines a surface position of a potential defect, and utilizes the 2D or 3D image data in determining whether an actual defect is present on the surface of the food object at the indicated surface position. The apparatus has an output unit for outputting defect related data in case both of the 2D and the 3D image data indicate that an actual defect is present on the surface of the food object at the indicated surface position.

13 Claims, 3 Drawing Sheets

(51) Int. Cl.
*A22C 17/00* (2006.01)
*G01N 33/12* (2006.01)

(56) References Cited

U.S. PATENT DOCUMENTS

| | | | | |
|---|---|---|---|---|
| 6,271,520 | B1* | 8/2001 | Tao | G01N 21/3563 |
| | | | | 250/910 |
| 6,610,953 | B1* | 8/2003 | Tao | G01N 21/3563 |
| | | | | 209/11 |
| 2005/0261864 | A1* | 11/2005 | Edwards | G01B 11/04 |
| | | | | 702/127 |
| 2009/0080706 | A1* | 3/2009 | Tao | G06T 7/0004 |
| | | | | 382/110 |
| 2011/0050880 | A1* | 3/2011 | Bourg, Jr. | G06T 7/90 |
| | | | | 382/110 |
| 2015/0130927 | A1* | 5/2015 | Luxen | G01B 11/303 |
| | | | | 348/128 |
| 2020/0060294 | A1* | 2/2020 | Thoroddsen | A22B 5/0017 |
| 2021/0035276 | A1* | 2/2021 | Ago | G06T 7/62 |

OTHER PUBLICATIONS

International Search Report and Written Opinion from PCT Application No. PCT/EP2019/067625, dated Sep. 27, 2019.

* cited by examiner

DETECTING SURFACE CHARACTERISTICS OF FOOD OBJECTS

FIELD OF THE INVENTION

The present invention relates to detecting surface characteristics of food objects. More particularly, it relates to detecting defects on the surface of the food objects while the food objects are being transported on a conveyor.

BACKGROUND OF THE INVENTION

Inspection systems for surface detection of e.g. blood spots or melanin spots on food objects are known wherein either a 2D imaging device or a 3D imaging device is used. A common problem with such surface detection is that false positives, i.e. wrong indications of defects present on the scanned surface, are relatively common. For example, a 2D scan of the surface may detect a colour difference over a certain region and it is uncertain judging from this data whether the indicated defect is a blood discolouration or a hole or a shadow or an indentation/recess.

SUMMARY OF THE INVENTION

The present invention aims to provide an apparatus and a method for detecting surface characteristics on incoming food objects that may be conveyed by a conveyor apparatus. The food objects may be of any suitable shape and type.

A first imaging device is provided for capturing two-dimensional image data (2D) pertaining to the food objects and a second imaging device for capturing three-dimensional image data (3D) of the food objects. At least one image processing unit is configured to utilize either one of the 2D or the 3D image data in determining whether a potential defect is present on the surface of the food object. The image processing unit may comprise a computer running image processing data software and having access to the image data stored in a computer memory. The image processing unit further determines a surface position of the potential defect, in case such a potential defect property is detected. To determine whether the potential defect is actually a defect and not a surface anomaly, such as a hole or recess, the image processing unit utilizes the remaining one of the 2D or the 3D image data in determining whether an actual defect is present on the surface of the incoming food object at the earlier determined surface position. An output unit may indicate whether an actual defect is present on the surface of the incoming food object at the determined surface position by outputting defect related data in case both of the 2D and the 3D image data indicate that is the case.

The first imaging device may be arranged to acquire the 2D image data before the second imaging device acquires the 3D image data. The first imaging device may as an example comprise any type of a digital camera that captures 2D surface image of the food objects, and the second imaging device may e.g. comprise a line scanner comprising a laser source that emits a 2D laser line on the surface and where a camera detects the reflected light and converts it into a 3D image. Other imaging device well known to a person skilled in the art may of course just as well be implemented.

The surface position may in one embodiment be determined via pixel scanning where via pixel illumination contrast said surface position may be determined.

Alternatively, the second imaging device may be arranged to acquire the 3D image data before the first imaging device acquires the 2D image data.

In an embodiment the first imaging device and the second imaging device may be arranged to simultaneously acquire the 2D image data and the 3D image data, respectively.

Thus, either the 2D data is first analyzed and any anomalies are flagged and their surface positions determined by the image processing unit whereafter the 3D data is analyzed and anomalies flagged. The 2D anomalies are then compared with the 3D anomalies so that the image processing unit can determine whether the anomaly was a true anomaly or a false anomaly. 2D anomalies means possible defaults detected in two-dimensional image data and 3D anomalies means possible defaults detected in three-dimensional image data.

Alternatively, the 3D data is first analyzed, and any anomalies are flagged by the image processing unit and their surface positions determined whereafter the 2D data is analyzed and anomalies flagged. The 3D anomalies are then compared with the 2D anomalies so that the image processing unit can determine whether the anomaly was a true anomaly or a false anomaly.

The 2D data and 3D data may also be analyzed concurrently and anomalies flagged in one data set are compared to the corresponding data set of the other dimensional type.

A further alternative is to use an imaging device that is able to acquire both 2D as well as 3D image data concurrently, thus combining the first imaging device and the second imaging device into one imaging device.

A method for detecting surface characteristics on incoming food objects that may be conveyed by a conveyor apparatus according to the invention comprises the steps of:
  capturing two-dimensional image data (2D) of a food object using a first imaging device and capturing three-dimensional image data (3D) of the food object using a second imaging device,
  using at least one image processing unit to process either one of the 2D or the 3D image data to determine whether a potential defect is present on the surface of the incoming food object, and in case such a potential defect property is detected, determine a surface position of the potential defect, and
  using the at least one image processing unit to process the remaining one of the 2D or the 3D image data to determine whether an actual defect is present on the surface of the incoming food object at the determined surface position,
  optionally outputting defect related data in case both of the 2D and the 3D image data indicate that an actual defect is present on the surface of the incoming food object at the surface position, using an output unit.

The first imaging device may in one embodiment be arranged to acquire the 2D image data before the second imaging device acquires the 3D image, or vice versa, first acquire the 3D data and subsequently the 2D data.

Alternatively, the first imaging device and the second imaging device are arranged to concurrently acquire the two-dimensional image data and the three-dimensional image data.

An advantage of the apparatus and method according to the invention is that false positives, i.e. a wrong indication of a defect present on the scanned surface, may be minimized or even totally avoided. For example, a 2D scan of the surface may detect a colour difference over a certain region, it is uncertain judging from this data whether the indicated defect is a blood discolouration or a hole or a shadow or an indentation/recess. The 3D data obtained from the 3D scan will unambiguously be able to ascertain whether the defect indicated by the 2D data is an actual defect or an indentation or recess present on the surface of the food product.

BRIEF DESCRIPTION OF THE DRAWINGS

The aspects and optional details of the invention will be explained below with reference to the drawings. In the drawings.

DESCRIPTION OF EMBODIMENTS

Figure 1:
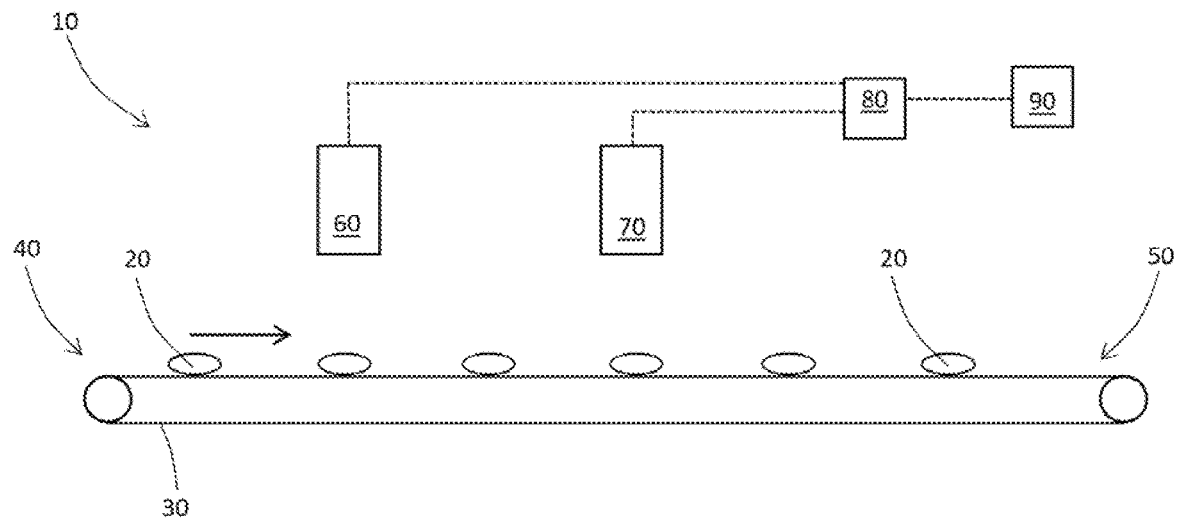
FIGS. 1 and 2 show two embodiments of a detecting apparatus according to an embodiment of the invention.

FIG. 1 schematically depicts a detecting apparatus 10 according to an embodiment of the invention. Food objects 20 are in this embodiment transported on a conveyor system 30 in a conveying direction as indicated by the arrow from an infeed end 40 to an outfeed end 50. The apparatus 10 comprises a first imaging device 60 for capturing two-dimensional image data (2D) of the food objects, and a second imaging device 70 for capturing three-dimensional image data (3D) of the food objects 20. The imaging device may be arranged adjacent the transport path of the conveyor system 30 so that the imaging devices 60, 70 may obtain their respective images of the food object 20 passing by the respective imaging device.

In FIG. 1 the 2D imaging device 60 is shown upstream of the 3D imaging device 70, with respect to the travel direction of the food objects 20 on the conveyor system 30. Alternatively, and still according to the invention, the 3D imaging system 70 may be arranged upstream of the 2D imaging system 60 (not shown). The imaging devices 60, 70 may be arranged in any position relative to the food objects 20 as long as they can obtain the image data associated with each food object.

The obtained image data (2D and 3D) are processed in at least one image processing unit 80 which may comprise a computer running image processing data software and having access to the image data stored in a computer memory.

The at least one image processing unit 80 may utilize the 2D image data in determining whether a potential defect is present on the surface of the food object 20. In case such a potential defect property is detected, the processing unit determines a surface position of the potential defect on the food object. Following this, the at least one image processing unit 80 may utilize the 3D image data in determining whether an actual defect is present on the surface of the food object within the determined surface position. For example, the 2D image data may indicate a discoloration at a certain surface location on the food object. The 3D image data may then be utilized to ascertain whether the discoloration is a void (hole or shadow or recess) in the surface or an actual discoloration (e.g. a blood stain).

The at least one image processing unit 80 may utilize an output unit 90, e.g. a display or an automatic message, for outputting defect related data in case both of said 2D and said 3D image data indicate that an actual defect is present on the surface of the food object within the surface position.

Alternatively, the at least one image processing unit 80 may utilize the 3D image data in determining whether a potential defect is present on the surface of the food object 20. In case such a potential defect property is detected, the processing unit determines a surface position of the potential defect on the food object. Following this, the at least one image processing unit 80 may utilize the 2D image data in determining whether an actual defect is present on the surface of the food object within the determined surface position. For example, the 3D image data may indicate a void (hole or shadow or recess) at a certain surface location on the food object. The 2D image data may then be utilized to ascertain whether the void (hole or shadow or recess) in the surface is an actual discoloration (e.g. a blood stain).

Figure 2:
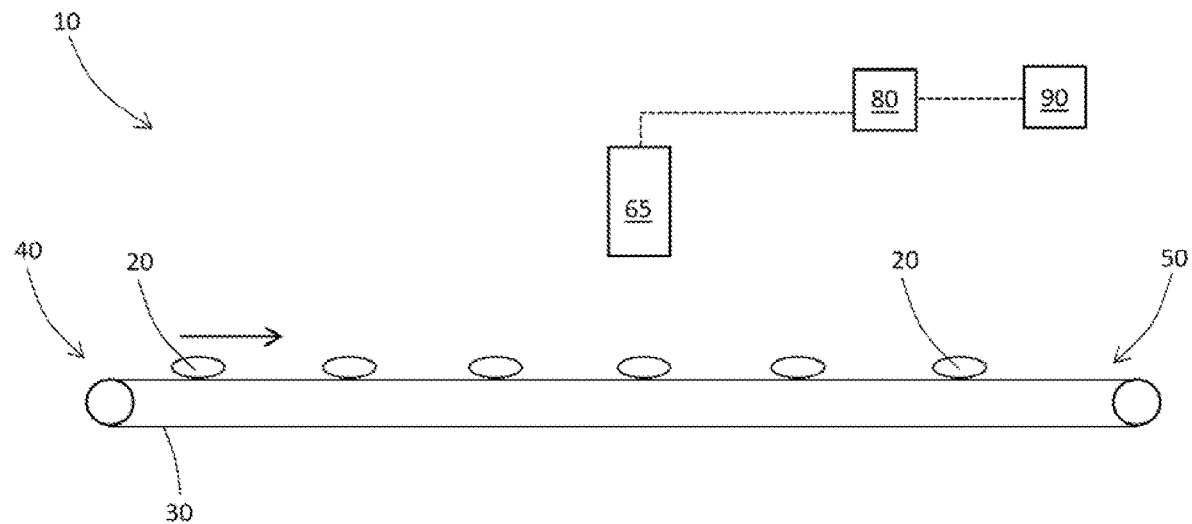

A further embodiment of the invention is shown in FIG. 2, where the apparatus utilizes an imaging device 65 that is able to acquire both 2D as well as 3D image data concurrently, thus combining the first imaging device and the second imaging device into one imaging device. All other technical features are similar to what is shown in FIG. 1 and keep the same reference numbers. The 2D data set and the 3D data set is manipulated as has been disclosed above for the embodiment according to FIG. 1.

Figure 3A:
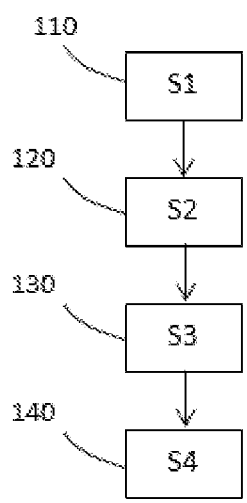
FIGS. 3A to 3C show flowcharts of embodiments of a method according to the present invention for detecting surface characteristics on food objects.
Figure 3B:
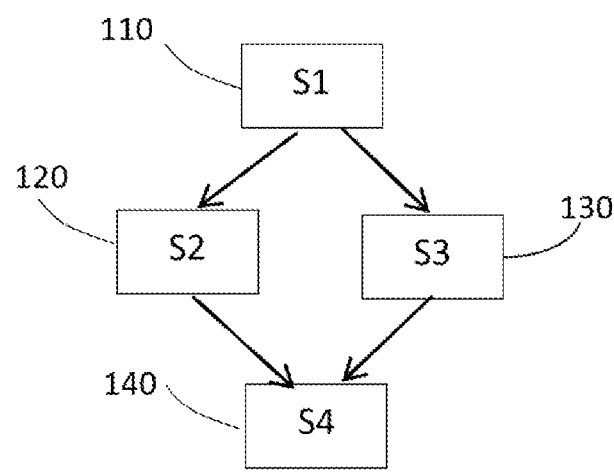
Figure 3C:
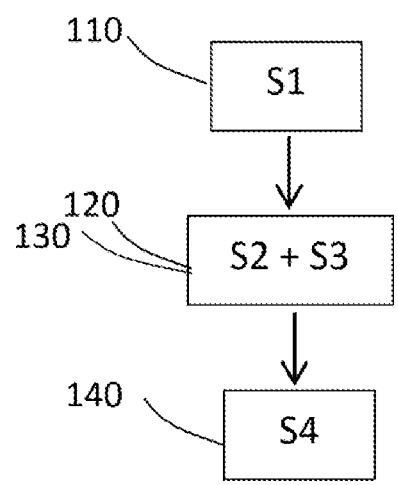
Figure 4A:
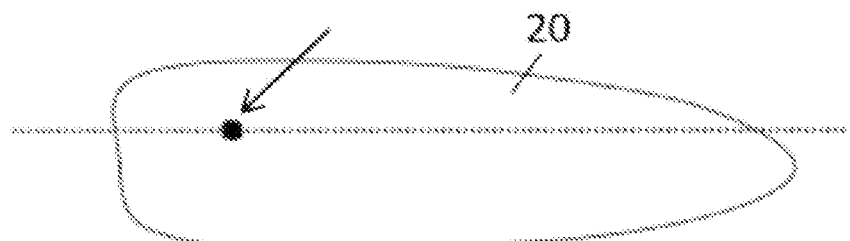
FIGS. 4A to 4D and FIGS. 5A and 5B show objects (20) analyzed with 2D image data and 3D image data.
Figure 4B:
Figure 4C:
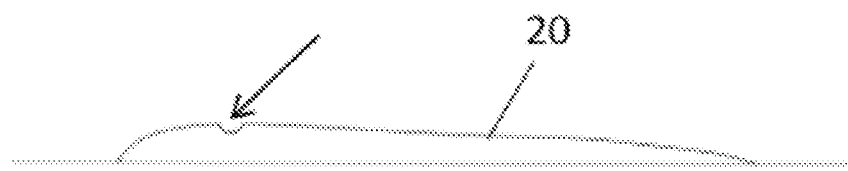
Figure 4D:
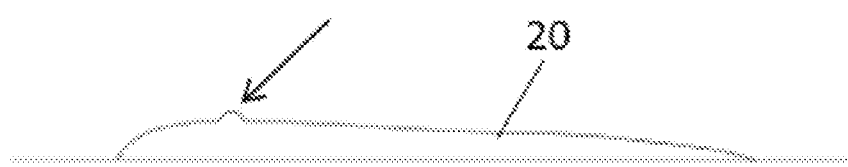

FIGS. 3A to 3C show different flowcharts of embodiments of a method according to the present invention for detecting surface characteristics on food objects, where the objects may be conveyed by a conveyor apparatus.

In step (S1) 110, two-dimensional image data (2D) of a food object 20 is captured using a first imaging device, and three-dimensional image data (3D) of the food object is captured using a second imaging.

In step (S2) 120, either one of the 2D or the 3D image data is processed to determine whether a potential defect is present on the surface of the food object, where in case such a potential defect property is detected, a surface position of the potential defect is determined.

In step (S3) 130, the remaining one of the 2D or the 3D image data is processed to determine whether an actual defect is present on the surface of the food object within the determined surface position.

In step (S4) 140, defect related data is output in case both of the 2D and the 3D image data indicate that an actual defect is present on the surface of the food object within the determined surface position.

FIG. 3A indicates one type of image data is processed in step S2 and afterwards the other type of image data is processed in step S3, followed by an output in step S4.

FIGS. 3B and 3C indicate simultaneously processing of the two types image data either by different processors as in FIG. 3B or by one processor as in FIG. 3C where the 2D and 3D data is processed together.

FIGS. 4A to 4D show an object (20) analyzed with 2D data and possible different 3D data indicating positive or false-positive result from 2D data. A fish fillet is conveyed along imaging devices for capturing two-dimensional image data and three-dimension image data. The fish fillet is located flat on the conveyor belt. In situation A, a 2D image illustrates the fish fillet seen from above. A black spot is identified. An arrow points towards this spot. The black spot indicates a possible defect of the fish fillet, this defect may e.g. be a blood spot, a melanin spot, a hole or something positioned onto the fish fillet. The dotted line indicates the location of the view along the fish fillet which is obtained from the 3D data and shown in the three independent situations illustrated by B to D.

Situation B illustrates no defect at the surface position of the fish fillet as detected by 2D data (arrow points to this surface position). As no defect is determined based on the acquired 3D data, there is no defects inside the fish fillet nor on the surface of the fish fillet and the 2D data indicated a positive result and the spot identified may be e.g. a blood spot or melanin spot.

Situation C illustrates a hole in the fish filled (indicated by the arrow) at the surface position of the black spot as detected from the acquired 2D data. If holes in the fish fillet are accepted the 3D data indicates a false-positive result obtained from the 2D data.

Situation D illustrates something located on the surface of the fish fillet as indicated by the arrow. This may be e.g. a small piece of fish material released from a fish during the processing steps performed before detecting surface characteristics of the fish fillets. Here the fish material stick to the fish fillet and looks like a small bubble on the fish fillet. The material on the fish fillet is not a default of the fish fillet and hereby the 3D data indicates a false-positive result obtained from the 2D data.

Figure 5A:
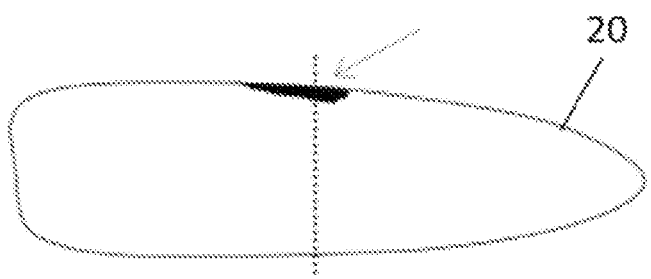
Figure 5B:

FIGS. 5A and 5B show an object analyzed with 2D data and where 3D data supplies further data to the result from 2D data which may be because of shadow due to the form of the object. In situation A, a fish fillet is conveyed along an imaging device for capturing two-dimensional image data. The fish fillet is located flat on the conveyor belt and the 2D image illustrates the fish fillet seen from above. A black area is identified. An arrow points towards this area. The black area indicates a possible defect of the fish fillet. The dotted line indicates the location of the view along the fish fillet which is obtained from the 3D data and shown in the situation illustrated in B.

Situation B obtained from 3D data illustrates no hole or dirt on the fish fillet, but it shows that the defect are found on a steep part of the fillet. As can be seen in situation B the fish fillet is higher in the left part than in the middle and right part and hereby the fish fillet may not be evenly illuminated when the imaging device capturing two-dimensional image data acquires data. The area which is shadowed may in the 2D data be indicated as a black area, and hereby the 3D data indicates a false positive result obtained from the 2D data.

The above description of possible embodiments of the present invention should not be interpreted as limiting the scope of the present invention.

The invention claimed is:

1. An apparatus for detecting surface characteristics on incoming food objects, comprising:
    a first imaging device for capturing two-dimensional image data and a second imaging device for capturing three-dimensional image data of a food object;
    at least one image processing unit configured to:
        utilize either one of said 2D or said 3D image data in determining whether a potential defect is present on the surface of said incoming food object, where, in case such a potential defect property is detected, determining a surface position of said potential defect;
        utilize the remaining one of said 2D or said 3D image data in determining whether an actual defect is present on the surface of said incoming food object at said determined surface position; and
        in case the potential defect property is detected and no actual defect is present, indicate a false-positive result of the actual defect obtained from the 2D image data, the false-positive result being defined as a wrong indication of the actual defect on the surface of said incoming food object;
    an output unit for outputting defect related data in case both of said 2D and said 3D image data indicate that an actual defect is present on the surface of said incoming food object at said determined surface position.

2. The apparatus according to claim 1, wherein the first imaging device is arranged to acquire the two-dimensional image data before the second imaging device acquires the three-dimensional image data.

3. The apparatus according to claim 1, wherein the second imaging device is arranged to acquire the three-dimensional image data before the first imaging device acquires the two-dimensional image data.

4. The apparatus according to claim 1, wherein the first imaging device and the second imaging device are arranged to concurrently acquire the two-dimensional image data and the three-dimensional image data.

5. The apparatus according to claim 1, wherein said incoming food objects are conveyed by a conveyor apparatus while said surface detection takes place.

6. A method for detecting surface characteristics of food objects, comprising the steps of:
    capturing two-dimensional image data of a food object using a first imaging device and capturing three-dimensional image data of the food object using a second imaging device,
    using at least one image processing unit to process either one of said 2D or said 3D image data to determine whether a potential defect is present on the surface of said incoming food object, and in case such a potential defect property is detected, determine a surface position of said potential defect and flag said potential defect for either one of said 2D or said 3D image data, and
    using the at least one image processing unit to process the remaining one of said 2D or said 3D image data to determine whether an actual defect is present on the surface of said incoming food object at said determined surface position; and
    in case the potential defect property is detected and no actual defect is present, indicating a false-positive result of the actual defect obtained from the 2D image data, the false-positive result being defined as a wrong indication of the actual defect on the surface of said incoming food object.

7. The method according to claim 6, wherein the method comprises a further step:
    outputting defect related data in case both of said 2D and said 3D image data indicate that an actual defect is present on the surface of said incoming food object at said determined surface position, using an output unit.

8. The method according to claim 6, wherein the first imaging device is arranged to acquire the two-dimensional image data before the second imaging device acquires the three-dimensional image data.

9. The method according to claim 6, wherein the second imaging device is arranged to acquire the three-dimensional image data before the first imaging device acquires the two-dimensional image data.

10. The method according to claim 6, wherein the first imaging device and the second imaging device are arranged to concurrently acquire the two-dimensional image data and the three-dimensional image data.

11. An apparatus for detecting surface characteristics on incoming food objects, comprising:
    a first imaging device for capturing two-dimensional image data and a second imaging device for capturing three-dimensional image data of a food object;
    at least one image processing unit configured to:

utilize either one of said 2D or said 3D image data in determining whether a potential defect is present on the surface of said incoming food object, where, in case such a potential defect property is detected, determining a surface position of said potential defect;

utilize the remaining one of said 2D or said 3D image data in determining whether an actual defect is present on the surface of said incoming food object at said determined surface position; and in case the potential defect property is detected and no actual defect is present, indicate a false-positive result of the actual defect obtained from the 2D image data, the false-positive result being defined as a wrong indication of the actual defect on the surface of said incoming food object;

an output unit for outputting defect related data in case both of said 2D and said 3D image data indicate that an actual defect is present on the surface of said incoming food object at said determined surface position;

wherein the first imaging device is arranged to acquire the two-dimensional image data before the second imaging device acquires the three-dimensional image data;

wherein the second imaging device is arranged to acquire the three-dimensional image data before the first imaging device acquires the two-dimensional image data.

12. The apparatus according to claim 11, wherein the first imaging device and the second imaging device are arranged to concurrently acquire the two-dimensional image data and the three-dimensional image data.

13. The apparatus according to claim 11, wherein said incoming food objects are conveyed by a conveyor apparatus while said surface detection takes place.

* * * * *